United States Patent [19]

Young et al.

[11] 4,169,777

[45] * Oct. 2, 1979

[54] PROCESS FOR PRODUCING AN ACTIVATED OXYGEN GAS SENSOR ELEMENT

[75] Inventors: Ching T. Young, Troy, Mich.; Donald J. Romine, Fostoria, Ohio; Phillip R. Woodruff, Tiffin, Ohio; Donald C. Davis, Fostoria, Ohio; James D. Bode, Royal Oak; Tseng Y. Tien, Ann Arbor, both of Mich.

[73] Assignee: Bendix Autolite Corporation, Fostoria, Ohio

[*] Notice: The portion of the term of this patent subsequent to Jan. 23, 1996, has been disclaimed.

[21] Appl. No.: 942,103

[22] Filed: Sep. 13, 1978

Related U.S. Application Data

[63] Continuation-in-part of Ser. No. 885,423, Mar. 13, 1978, Pat. No. 4,136,000.

[51] Int. Cl.² .................. C23G 1/02; G01N 27/58
[52] U.S. Cl. .................. 204/195 S; 134/41; 252/472
[58] Field of Search .................. 204/1 S, 195 S, 130; 123/119 E; 60/276; 252/472; 134/41

[56] References Cited

U.S. PATENT DOCUMENTS 4,136,000  1/1979  Davis et al. .................. 204/195 S

*Primary Examiner*—G. L. Kaplan
*Attorney, Agent, or Firm*—Raymond J. Eifler; William G. Kratz, Jr.

[57] ABSTRACT

An activated oxygen gas sensor element having an increased voltage output under rich gas conditions, short switching response and reduced internal resistance is produced by chemically treating the inner conductive catalyst electrode of the sensor element with an inorganic acid or acid salt and current activating the outer conductive catalyst electrode by applying a direct current to the sensor element, with the outer electrode as an anode, while the outer electrode is at an elevated temperature and in the presence of a nonoxidizing atmosphere.

16 Claims, No Drawings

PROCESS FOR PRODUCING AN ACTIVATED OXYGEN GAS SENSOR ELEMENT

CROSS-REFERENCE TO RELATED APPLICATION

This application is a continuation-in-part of an application entitled "Process for Producing Improved Solid Electrolyte Oxygen Gas Sensors," Ser. No. 885,423 filed Mar. 13, 1978 by the present inventors, and now U.S. Pat. No. 4,136,000, the contents of said application being incorporated by reference herein.

BACKGROUND OF THE INVENTION

As discussed in our earlier application, oxygen gas sensors containing solid electrolyte oxygen gas sensor elements are used to measure the oxygen content of an automotive exhaust gas for the purpose of regulating the efficiency of the engine through control of the air to fuel ratio. These generally thimble-shaped sensor elements having an inner conductive catalyst electrode on the inner surface of the thimble and an outer conductive catalyst electrode on the outer surface of the thimble are conductively connected to a monitoring and actuating system to adjust said air-fuel ratio.

In our earlier application, the use of a chemical treatment, wherein the inner electrode was contacted with an inorganic acid or acid salt, produced a chemical treatment of the inner electrode and resulted in an increased voltage output in the positive range for the sensor element and also reduced the internal resistance of the solid electrolyte sensor element, both of which are beneficial to the operation of the sensor. Also, as discussed therein, when the chemically activated sensor elements are also subjected to a current treatment, wherein the sensor element is subjected to a direct current, with the outer catalytic electrode as a cathode, and at an elevated temperature and in the presence of a reducing gas, the above properties are further enhanced and, in addition, the switching response time required for switching from rich to lean gas composition readings is reduced.

In using the combined chemical and current activation treatment of our previous application, however, the need for the presence of a reducing gas at the outer electrode during current activation was present, as well as the need for a recovery period during which the sensor element was maintained at the elevated temperature, in order to provide a stable condition within the solid electrolyte body.

We have now discovered that if current activation of the sensor element is combined with the chemical activation, where the current activation is carried out by applying a direct current to the sensor element, with the outer electrode as an anode, only a nonoxidizing gas need be present and, in addition, the need for a recovery period is removed, where short time periods of current application are used.

SUMMARY OF THE INVENTION

An activated oxygen gas sensor element having an increased voltage output under rich gas conditions, shortened switching response time and reduced internal resistance, where the element comprises a solid electrolyte body, such as zirconium dioxide, having an inner conductive catalyst electrode on the inner surface and an outer conductive catalyst electrode on the outer surface, is produced by contacting the inner conductive catalyst electrode with an inorganic acid or acid salt and by applying a direct current to the sensor element, with the outer electrode as an anode, with the current application effected while the outer electrode is in the presence of a nonoxidizing atmosphere and at a temperature in excess of 450° C., the current density thereof being at least 5 milliamperes per square centimeter of the planar surface of the outer conductive catalyst electrode.

DETAILED DESCRIPTION

The gas sensor elements that are subjected to the present process to improve the properties thereof are generally in the shape of a closed tubular member, thimble like, with the sensor body formed of a solid electrolyte material, such as stabilized zirconium dioxide. This general shape of the electrolyte body is known in the art, as well as the solid electrolyte usable. The thimble-like shape of such sensor element, having a shoulder at the open end thereof, is illustrated in U.S. Pat. No. 3,978,006 and other existing publications, which also describe various solid electrolyte materials useful in forming such sensor elements. The preferred composition for forming the solid electrolyte body is a mixture of zirconium dioxide and stabilizing materials such as calcium oxide or yttrium oxide.

To the interior surface of the electrolyte body, an inner electrode of conductive catalyst material is applied, such as by the coating of the surface with a platinum paste with or without a glass frit or other high temperature-resistance bonding material. This paste coating generally covers the interior surface of the closed terminal end and extends to the shoulder of the electrolyte body. This combination is then fired at a temperature of 600°–1000° C. or higher, as is known in the art, for a sufficient period of time to convert the platinum paste to an electrically conductive inner electrode.

A glass frit or other bonding agent, when used, while providing excellent adherence of the catalytic electrode to the interior surface of the solid electrolyte body, has an effect of increasing the internal electrical resistance of the sensor, reducing the positive output voltage of the sensor when the external surface thereof is exposed to a rich atmosphere and also causing a negative voltage output when the external surface thereof is exposed to a lean atmosphere.

As described in our co-pending parent application, Ser. No. 885,423, the conductive catalyst electrode on the interior surface of the solid electrolyte body is subjected to a chemical activation treatment to improve the voltage output and to reduce the internal resistance of the sensor element. The treatment of the inner conductive catalyst electrode is by contact of the surface thereof with a solution of an inorganic acid or an acid salt. Solutions of an inorganic acid, such as hydrochloric acid, sulfuric acid, nitric acid, phosphoric acid, hydrofluoric acid and chloroplatinic acid, are preferred while acid salts, such as ammonium chloride, hydroxylamine hydrochloride, ammonium chloroplatinate or the like, are also usable.

In treating the conductive catalyst electrode with an acidic or acid salt solution, the electrode may be contacted with the solution and the same held in contact for a period of time before removing the solution and rinsing, or the electrode in contact with the solution may be heated to evaporate solvent from the solution and then heated further to elevated temperatures in the range of up to 1200° C.

In addition to the aforedescribed chemical activation of the sensor element inner electrode, the outer electrode is subjected to a current activation treatment.

Both conductive catalyst electrodes, as is known, may comprise platinum or a platinum family-metal catalyst, such as palladium, rhodium or mixtures thereof, with the preferred material being platinum.

In the current activation treatment step of the present invention, a direct current is applied to the sensor element, with the outer conductive catalyst electrode as an anode, in the presence of a nonoxidizing gas and at an elevated temperature. This current activation is described in detail in the application of one of the inventors hereof, Ching T. Young, entitled "Process for Producing a Solid Electrolyte Oxygen Gas Sensing Element," Ser. No. 942,102, filed on even date herewith, the contents of said application being incorporated by reference herein. As described in said co-pending application, filed on even date herewith, the outer surface of the solid electrolyte body, with the outer conductive catalytic electrode thereon, is subjected to a nonoxidizing atmosphere, and while the outer surface is at a temperature in excess of 450° C., a direct current is applied to the sensing element, with the outer electrode as an anode, the current density thereof being at least 5 milliamperes per square centimeter of the planar surface of said outer conductive catalyst electrode.

The nonoxidizing atmosphere, to which the outer electrode is subjected, during the current activation step may be a reducing, neutral or inert atmosphere, provided that the atmosphere is nonoxidizing. Carbon monoxide, hydrogen or rich exhaust gas mixtures are examples of reducing atmospheres, while nitrogen is the preferred neutral gas, and argon is an example of an inert gas. Mixtures of a reducing gas and a neutral or inert gas may, of course, be used, and a small amount of water vapor may also be present in the gaseous mixture.

The temperature to which the outer surface is heated prior to application of the direct current is about 450° C. and may be as high as about 1100° C. depending upon the solid electrolyte used and the other process conditions. A preferred temperature range of 600°–900° C. provides an economical and efficient temperature range for the current activation.

Application of the direct current is made, to the sensor element, with the outer conductive catalytic electrode at the elevated temperature and in the presence of a nonoxidizing gas, with the outer electrode as an anode and the inner conductive catalytic electrode as a cathode. A direct current power source is thus connected to the conductive catalyst electrodes, with the outer electrode connected to the positive terminal and the inner electrode connected to the negative terminal of the power source.

The current charge usable in the current activation step is one which provides a current density of at least 5 milliamperes per square centimeter of the planar surface of the outer conductive catalyst electrode. The term "current density," as used herein, is determined by dividing the current (in milliamperes) by the planar surface area of the outer conductive catalyst electrode (cm$^2$) on the outer surface of the solid electrolyte body, while the term "planar surface of the outer electrode" is used to define the surface that would be present if the conductive catalyst electrode were a smooth coating without porosity. The preferred range of current density is between 20–150 milliamperes per square centimeter of the outer conductive catalyst electrode surface. Current densities below 5 milliamperes/cm$^2$ are ineffective to give the beneficial results and, while much higher current densities can be used, higher current densities far above the preferred range can cause fracturing of the element through shock.

The application of the direct current, as above described, for a period of only about two seconds has been found to provide the desired properties, while a time of current application of six seconds to about ten minutes is preferred. The longer times of current application, however, may require a recovery period for stabilization of the solid electrolyte. Such a recovery period is effected by maintaining the outer surface of the sensor element in the presence of a nonoxidizing gas and at the elevated temperature for a period of time after the current is turned off.

The following examples further illustrate the present invention. In these examples, the testing of thimbles, as sensor elements, to determine their performance in terms of voltage output under rich and lean conditions, the switching response to gas variation and their internal resistance, was made by inserting the thimbles into protective housings with conductive leads connected to the inner and outer electrodes to form sensors. The tests were conducted at 350° C. and at 800° C. with testing at 800° C. effected first.

The sensor performance tests were conducted by inserting the sensors into a cylindrical metal tube and exposing them to oxidizing and reducing gaseous atmospheres within the tube through use of a gas burner adjustable to produce such atmospheres. Sensors placed in the desired positions in the tube were heated to testing temperature and the voltage output measured using a volt meter. The output was also connected to an oscilloscope to measure the speed of response of the sensor when the burner flame is changed from rich to lean and from lean to rich. A routine test consisted of setting the flame to rich condition, measuring the voltage output of the sensor, switching the flame suddenly to lean condition, triggering the oscilloscope sweep at the same time to record the rich to lean switch of the sensor, switching the flame suddenly back to rich condition, again triggering the oscilloscope to record the sensor output change, and finally adjusting the flame to a lean condition and measuring the sensor output voltage. The switching time is defined as the time period required for the output voltage, as recorded on the oscilloscope, to sweep between 600 and 300 millivolts. When the sensor output voltage under rich gas condition is less than 600 millivolts, the switching response time is not determinable (n/d) according to the criteria used for this switching response measurement. Rich voltage output measurements were then made with different known values of shunting resistance across the sensor terminals. These measurements provided data for calculating the internal resistance of the sensors.

A series of gas sensor electrolyte body thimbles was prepared, for use in the following examples, from ball-milled zirconia, yttria and alumina, in a ratio of 80%, 14% and 6% by weight respectively, by isostatically pressing the same in the desired thimble shape and firing at high temperature.

EXAMPLE I

Three of the series of electrolyte body thimbles (AEN-1, AEN-2 and AEN-3) had an inner electrode applied to the inner surface thereof by coating the inner surface with a platinum suspension containing a glass frit for bonding purposes. The thimble with its inner electrode was then heated in an oxidizing atmosphere to burn off the organic constituents of the suspension and bond the platinum to the zirconia surface. The external platinum catalyst electrode was next applied to the outer surface of the thimble by known thermal vapor deposition. A porous ceramic coating was applied over the external catalyst layer for protection. The thimbles were then formed into sensors and tested as to voltage output, switching response and internal resistance, as hereinbefore described. The results of the tests are listed in Table I under the designation "No Treatment."

The thimbles were then subjected to chemical treatment by applying to the inner surface thereof an aqueous solution of one normal hydrochloric acid by filling the interior portion of the thimbles with the acid. The sensors were maintained at 50° C. for a thirty minute period, and the acid solution was then removed and the interior of the sensor element washed with distilled water and dried at 100° C. for at least one hour. These sensor elements were then again tested as to voltage output, switching response and internal resistance. The results of these tests are listed in Table I under the heading "After Chemical Treatment." After this testing was effected, the sensor elements were subjected to current activation as follows. The sensor elements, as sensors in a protective housing and with conductive leads, were inserted into a manifold with the outer surface of the sensor element, having the outer conductive catalyst coating thereon, exposed to a flow of reducing gas, 0.5% carbon monoxide in nitrogen (with 0.01 mg/cm³ water vapor), at a flow rate of 710 cm³/min. The elements were preheated to about 700° C. during a ten-minute period. The inner conductive catalyst electrode was in contact with air, and the temperature of the sensor was taken at the bottom of the inner region of the sensor element. The sensors were then subjected to a direct current, as indicated, for a ten-minute period, the direct current charge applied with the outer electrode as an anode at a current density of about 167 milliamperes/cm² of the outer electrode planar surface, with the gas flow continued. The direct current was then stopped and the sensor element allowed a recovery period of ten minutes at said temperature and with the outer electrode in said gas flow.

These sensor elements were then again tested as to voltage output, switching response and internal resistance. The results of these tests are listed in Table I under the heading "After Chemical Treatment and Current Activation."

TABLE I

| | | 350° Testing | | | | | 800° Testing | | | | |
|---|---|---|---|---|---|---|---|---|---|---|---|
| | | Voltage Output | | Switching Response | | Internal Resistance | Voltage Output | | Switching Response | | Internal Resistance |
| Sensor | Treatment | Rich (mv) | Lean (mv) | RL (ms) | LR (ms) | tance (kΩ) | Rich (mv) | Lean (mv) | RL (ms) | LR (ms) | tance (Ω) |
| AEN-1 | No Treatment | 125 | −306 | n/d | n/d | >1,000 | 800 | 54 | 25 | 30 | 121 |
| AEN-2 | No Treatment | 339 | −94 | n/d | n/d | >1,000 | 787 | 44 | 25 | 20 | 57 |
| AEN-3 | No Treatment | 330 | 30 | n/d | n/d | >1,000 | 778 | 33 | 20 | 20 | 65 |
| | After Chemical Treatment | | | | | | | | | | |
| AEN-1 | HCl | 906 | 160 | >1000 | 40 | 35 | 805 | 55 | 40 | 35 | 50 |
| AEN-2 | HCl | 909 | 150 | >1000 | 40 | 35 | 801 | 56 | 25 | 25 | 45 |
| AEN-3 | HCl | 901 | 147 | >1000 | 50 | 39 | 807 | 59 | 40 | 35 | 45 |
| | After Chemical Treatment & Current Activation | | | | | | | | | | |
| AEN-1 | Direct Current | 858 | −16 | 80 | 40 | 79 | 816 | 43 | 25 | 15 | 24 |
| AEN-2 | Direct Current | 947 | 13 | 80 | 40 | 23 | 818 | 58 | 25 | 15 | 15 |
| AEN-3 | Direct Current | 884 | −13 | 70 | 40 | 50 | 816 | 50 | 25 | 15 | 20 |

The tests results shown in Table I indicate the effect of the chemical treatment upon the voltage output and internal resistance of the sensor element, and also the effect of the combination of the chemical treatment and current activation upon the element, with resultant high voltage output, low internal resistance and significantly shortened response time.

EXAMPLE II

Three other thimbles of the series of electrolyte body thimbles (AP7-11, AP7-12 and AP7-13) had inner and outer electrodes applied thereto as such application was effected in Example I. These three sensor elements were then chemically treated by applying to the inner surface thereof a 2 N aqueous solution (2 gram equivalent per liter of solution) of hydrochloric acid. The inner thimble portion was filled with the acid to cover the inner electrode, the sensor heated to 50° C. for 0.5 hr. and, after pouring out the acid, the inner portion was rinsed twice with methanol. These three elements were then tested as to voltage output, switching response and internal resistance. The results of the tests are listed in Table II under the designation "Chem. Treated." These three sensor elements were then subjected to current activation by insertion into a manifold with the outer conductive catalyst coating exposed to a flow of nitrogen atmosphere (710 cm³/min.) while the elements were heated to 750° C. during a ten-minute period. At a temperature of 750° C., and with the outer electrode subjected to the nitrogen atmosphere, the sensor elements had applied thereto a direct current, with the outer electrode as an anode, the current density of which is listed in Table II for a period of ten minutes. The direct current was then stopped and the sensor elements allowed a recovery period of ten minutes, with the outer conductive catalytic electrode in the flow of nitrogen, and at the elevated temperature. These sensor elements were then again tested. The test results are listed in Table II under the heading "After Chemical Treatment and Current Activation."

TABLE II

| | 350° Testing | | | 800° Testing | | |
|---|---|---|---|---|---|---|
| | Voltage | Switching | Internal | Voltage | Switching | Internal |

TABLE II-continued

| Sensor | Treatment | Output Rich (mv) | Output Lean (mv) | Response RL (ms) | Response LR (ms) | Resistance (kΩ) | Output Rich (mv) | Output Lean (mv) | Response RL (ms) | Response LR (ms) | Resistance (Ω) |
|---|---|---|---|---|---|---|---|---|---|---|---|
| AP7-11 | Chem. Treated | 885 | 229 | 8,4000 | 60 | 56 | 808 | 89 | 30 | 45 | 39 |
| AP7-12 | Chem. Treated | 887 | 191 | 6,800 | 55 | 25 | 807 | 88 | 25 | 25 | 38 |
| AP7-13 | Chem. Treated | 857 | 276 | 7,900 | 70 | 70 | 820 | 85 | 30 | 55 | 38 |
| | After Chemical Treatment & Current Activition | | | | | | | | | | |
| | Current Density (ma/cm²) | | | | | | | | | | |
| AP7-11 | 100 | 748 | −132 | 85 | 165 | 57 | 799 | 63 | 25 | 25 | 13 |
| AP7-12 | 20 | 936 | 35 | 65 | 45 | 27 | 806 | 77 | 15 | 15 | 11 |
| AP7-13 | 8 | 944 | 122 | 600 | 55 | 21 | 792 | 78 | 15 | 15 | 13 |

As illustrated by the test results listed in Table II, the use of current densities as low as 8 ma/cm² for a ten-minute period at 750° C. are effective in shortening the response time of the sensor element following the present process, although the degree of improvement is not as great as when current densities of 20 or 100 ma/cm² are used.

EXAMPLE III

Four other of the series of electrolyte body thimbles (AP7-10, AP7-21, AP7-22 and AP7-23) had inner and outer electrodes applied thereto as such application was effected in Example I. These four sensor elements were then chemically treated following the procedure described in Example II. These four sensor elements were then tested. The results of the tests are listed in Table III under the designation "Chem. Treated." These four sensor elements were then subjected to current activation according to the procedure described in Example II, except that the current density used for each was 100 milliamperes/cm²; the temperature used for AP7-23 was 600° C.; and the time of application of the direct current as well as the recovery time were varied for the four sensors, these values being listed in Table III. These four sensor elements were again tested as to voltage output, switching response and internal resistance. The results of these tests are listed in Table III under the heading "After Chemical Treatment and Current Activation."

TABLE III

| | | 350° Testing | | | | | 800° Testing | | | | |
|---|---|---|---|---|---|---|---|---|---|---|---|
| | | Voltage Output | | Switching Response | | INternal Resistance | Voltage Output | | Switching Response | | Internal Resistance |
| Sensor | Treatment | Rich (mv) | Lean (mv) | RL (ms) | LR (ms) | (kΩ) | Rich (mv) | Lean (mv) | RL (ms) | LR (ms) | (Ω) |
| AP7-10 | Chem. Treated | 885 | 237 | 8,900 | 70 | 44 | 796 | 91 | 15 | 45 | 36 |
| AP7-21 | Chem. Treated | 782 | 224 | 6,200 | 70 | 102 | 811 | 82 | 25 | 50 | 44 |
| AP7-22 | Chem. Treated | 789 | 186 | 3,900 | 70 | 107 | 801 | 83 | 20 | 45 | 43 |
| AP7-23 | Chem. Treated | 797 | 269 | 7,300 | 120 | 106 | 806 | 86 | 30 | 55 | 40 |
| | After Chemical Treatment & Current Activation | | | | | | | | | | |
| Time of Current (min.) | Recovery Time (min.) | | | | | | | | | | |
| AP7-10 0.1 | 10 | 956 | 53 | 50 | 30 | 17 | 798 | 77 | 15 | 15 | 10 |
| AP7-21 0.1 | 0 | 957 | 42 | 40 | 30 | 15 | 799 | 80 | 20 | 15 | 12 |
| AP7-22 0.03 | 0 | 932 | 89 | 390 | 50 | 27 | 784 | 88 | 20 | 15 | 20 |
| AP7-23 0.1 | 0 | 915 | 94 | 180 | 40 | 28 | 793 | 87 | 15 | 15 | 16 |

As shown by the test results, where a short time of current application is used, for example, 0.1 or 0.03 minute, the need for a recovery period is obviated and the sensor elements do not appear to require stabilization after such treatment in order to provide sensor elements of significantly improved properties.

EXAMPLE IV

Seven additional thimbles of the series of electrolyte body thimbles, (AP7-15, AP7-14, AP7-16, AP7-17, AP7-19, AP7-18 and AP7-20) had inner and outer electrodes applied as in Example I and were chemically treated following the procedure described in Example II. These seven sensor elements were then tested as to voltage output, switching response and internal resistance. The results of the tests are listed in Table IV under the designation "Chem. Treated." The seven sensor elements were then current activated according to the procedure described in Example II, except that the temperature for activation, the current density, and the time of passing of the direct current were varied for particular of the sensor elements as indicated in Table IV. The preheating time and recovery time were both ten minutes in each case. The seven sensor elements were then again tested. The results of these tests are listed in Table IV under the heading "After Chemical Treatment and Current Activation."

TABLE IV

| | 350° Testing | | | | 800° Testing | | | | |
|---|---|---|---|---|---|---|---|---|---|
| | Voltage Output | | Switching Response | | Internal Resistance | Voltage Output | | Switching Response | | Internal Resistance |
| | Rich | Lean | RL | LR | tance | Rich | Lean | RL | LR | tance |

TABLE IV-continued

| Sensor | Treatment | (mv) | (mv) | (ms) | (ms) | (kΩ) | (mv) | (mv) | (ms) | (ms) | (Ω) |
|---|---|---|---|---|---|---|---|---|---|---|---|
| AP7-15 | Chem. Treated | 820 | 176 | 6,500 | 70 | 61 | 796 | 84 | 20 | 35 | 39 |
| AP7-14 | Chem. Treated | 893 | 196 | 5,500 | 70 | 17 | 787 | 78 | 15 | 50 | 50 |
| AP7-16 | Chem. Treated | 802 | 247 | 4,600 | 65 | 97 | 803 | 89 | 20 | 45 | 34 |
| AP7-17 | Chem. Treated | 798 | 245 | 6,000 | 90 | 108 | 808 | 86 | 30 | 45 | 42 |
| AP7-19 | Chem. Treated | 854 | 237 | 4,600 | 60 | 44 | 797 | 81 | 25 | 45 | 39 |
| AP7-18 | Chem. Treated | 818 | 212 | 4,100 | 60 | 76 | 767 | 92 | 15 | 40 | 35 |
| AP7-20 | Chem. Treated | 887 | 288 | 7,200 | 60 | 72 | 812 | 79 | 25 | 55 | 42 |

After Chemical Treatment & Current Activation

| | Temp. °C. | (Current) Den. (ma/cm$^2$) | Time (min.) | | | | | | | | | |
|---|---|---|---|---|---|---|---|---|---|---|---|---|
| AP7-15 | 600 | 100 | 0.17 | 923 | 87 | 170 | 40 | 24 | 794 | 89 | 15 | 15 | 15 |
| AP7-14 | 600 | 100 | 10 | 878 | −1 | 55 | 50 | 24 | 802 | 80 | 20 | 15 | 10 |
| AP7-16 | 600 | 20 | 10 | 931 | 54 | 85 | 40 | 26 | 794 | 84 | 15 | 10 | 11 |
| AP7-17 | 600 | 8 | 10 | 922 | 99 | 900 | 40 | 21 | 788 | 86 | 15 | 15 | 20 |
| AP7-19 | 450 | 100 | 0.1 | 857 | 121 | 2,800 | 50 | 47 | 794 | 85 | 20 | 35 | 41 |
| AP7-18 | 450 | 100 | 10 | 925 | 95 | 720 | 45 | 33 | 774 | 86 | 15 | 15 | 23 |
| AP7-20 | 450 | 20 | 10 | 852 | 142 | 1,200 | 70 | 49 | 774 | 81 | 20 | 25 | 24 |

The results listed in Table IV illustrate the effect of various temperatures, current densities and times of current application on the sensor properties. While the use of 450° C. in the test listed did not produce acceptable sensors for operational purposes, it should be noted that these sensors had inner electrodes of fluxed platinum (containing a glass or other bonding material) and the use of such a temperature where no flux is used on the inner electrode would provide the shortening of the switching response time desired.

The present process provides a combined chemical and current treatment of solid electrolyte sensor elements which results in sensor elements of improved properties of high voltage output under rich conditions, fast response time and low internal resistance, all such properties of which result in an efficient, economical and stable operation of oxygen gas sensors containing such elements.

What is claimed is:

1. A process for producing an activated oxygen gas sensor element having an increased voltage output under rich gas conditions, shortened switching response time and reduced internal resistance, wherein the sensor element comprises a solid electrolyte body having an inner conductive catalyst electrode on the inner surface and an outer conductive catalyst electrode on the outer surface thereof, comprising:
   (a) contacting said inner conductive catalyst electrode with an acidic reactant selected from the group consisting of inorganic acids and acid salts; and
   (b) applying a direct current to the sensor element, with said outer conductive catalyst electrode as an anode, while subjecting said outer conductive catalyst electrode to a nonoxidizing atmosphere at an elevated temperature in excess of 450° C., the current density thereof being at least 5 milliamperes per square centimeter of the planar surface of said outer conductive catalyst electrode.

2. The process for producing an activated oxygen gas sensor element as defined in claim 1 wherein said nonoxidizing gas is selected from the group consisting of reducing gases, neutral gases, inert gases and mixtures thereof.

3. The process for producing an activated oxygen gas sensor element as defined in claim 2 wherein said nonoxidizing gas is a reducing gas.

4. The process for producing an activated oxygen gas sensor element as defined in claim 2 wherein said nonoxidizing gas is a neutral gas.

5. The process for producing an activated oxygen gas sensor element as defined in claim 4 wherein said neutral gas is nitrogen.

6. The process for producing an activated oxygen gas sensor element as defined in claim 1 wherein said current density is between 20-150 milliamperes per square centimeter of the planar surface of said outer conductive catalyst electrode.

7. The process for producing an activated oxygen gas sensor element as defined in claim 1 wherein said elevated temperature is between 600°-900° C.

8. The process for producing an activated oxygen gas sensor element as defined in claim 1 wherein said direct current is applied for a period of time between six seconds and ten minutes.

9. The process for producing an activated oxygen gas sensor element as defined in claim 1 wherein, following application of said current, said sensor element is maintained at said temperature for a period of time.

10. The process for producing an activated oxygen gas sensor element as defined in claim 1 wherein said solid electrolyte body comprises zirconium dioxide.

11. The process for producing an activated oxygen gas sensor element as defined in claim 1 wherein said inner conductive catalyst electrode and said outer conductive catalyst electrode comprise platinum.

12. The process for producing an activated oxygen gas sensor element as defined in claim 11 wherein said inner conductive catalyst electrode is bonded to said solid electrolyte body by a glass frit.

13. The oxygen gas sensor element produced according to the process of claim 1.

14. A process for producing an activated oxygen gas sensor element having an increased voltage output under rich gas conditions, shortened switching response time and reduced internal resistance, wherein the sensor element comprises a zirconium dioxide body having an inner platinum electrode on the inner surface and an outer platinum electrode on the outer surface thereof, comprising:
   (a) contacting said inner platinum electrode with an acidic reactant selected from the group consisting of inorganic acids and acid salts; and
   (b) applying a direct current to the sensor element, with said outer platinum electrode as an anode, while subjecting said outer platinum electrode to a nonoxidizing atmosphere at an elevated temperature between 600°–900° C., the current density thereof being between 20–150 milliamperes per square centimeter of the planar surface of said outer platinum electrode.

15. The process for producing an activated oxygen gas sensor element as defined in claim 14 wherein said nonoxidizing atmosphere comprises nitrogen.

16. The oxygen gas sensor element produced according to the process of claim 14.

* * * * *